United States Patent [19]
Mercuri et al.

[11] Patent Number: 6,022,354
[45] Date of Patent: Feb. 8, 2000

[54] BONE HARVESTING COLLECTION AND DELIVERY SYSTEM

[76] Inventors: Gregory M. Mercuri, 1421 Berne La., Lewisville, Tex. 75067; Rick A. Buss, 2812 Rosedale, University Park, Tex. 75205

[21] Appl. No.: 09/205,953

[22] Filed: Dec. 4, 1998

[51] Int. Cl.[7] .................................................. A61B 17/16
[52] U.S. Cl. ............................................ 606/80; 606/96
[58] Field of Search .................................. 606/80, 83, 84, 606/86, 96

[56] References Cited

U.S. PATENT DOCUMENTS 5,694,951  12/1997  Bonutti ..................................... 606/80

Primary Examiner—Michael Buiz
Assistant Examiner—Daphna Shai
Attorney, Agent, or Firm—Richard K. Thomson

[57] ABSTRACT

A drill bit configured for maximum bone penetration harvests and morselizes bone fragments from a harvest site for use in reparative bone grafting. A suction port on a removable harvest cap enables the bone fragments and irrigation fluids to be drawn into a distal end of a cannula portion of a collection reservoir. A filter screen mounted within the chamber of the collection reservoir enables the irrigation fluids to be removed while the bone fragments are retained in the reservoir. A retention plug can be inserted into the distal end of the cannula to allow the removable cap and drill to be removed. The reservoir can be transported to a reparation site, the retention plug removed and a plunger inserted into the open upper end of the collection reservoir to deliver morselized bone fragments out of the distal end of the cannula to the site to be restored. By replacing the harvesting cap with a collection cap which has a larger suction port, the system can be optimized for recovering morselized bone fragments which have been harvested by an earlier drilling operation.

15 Claims, 3 Drawing Sheets

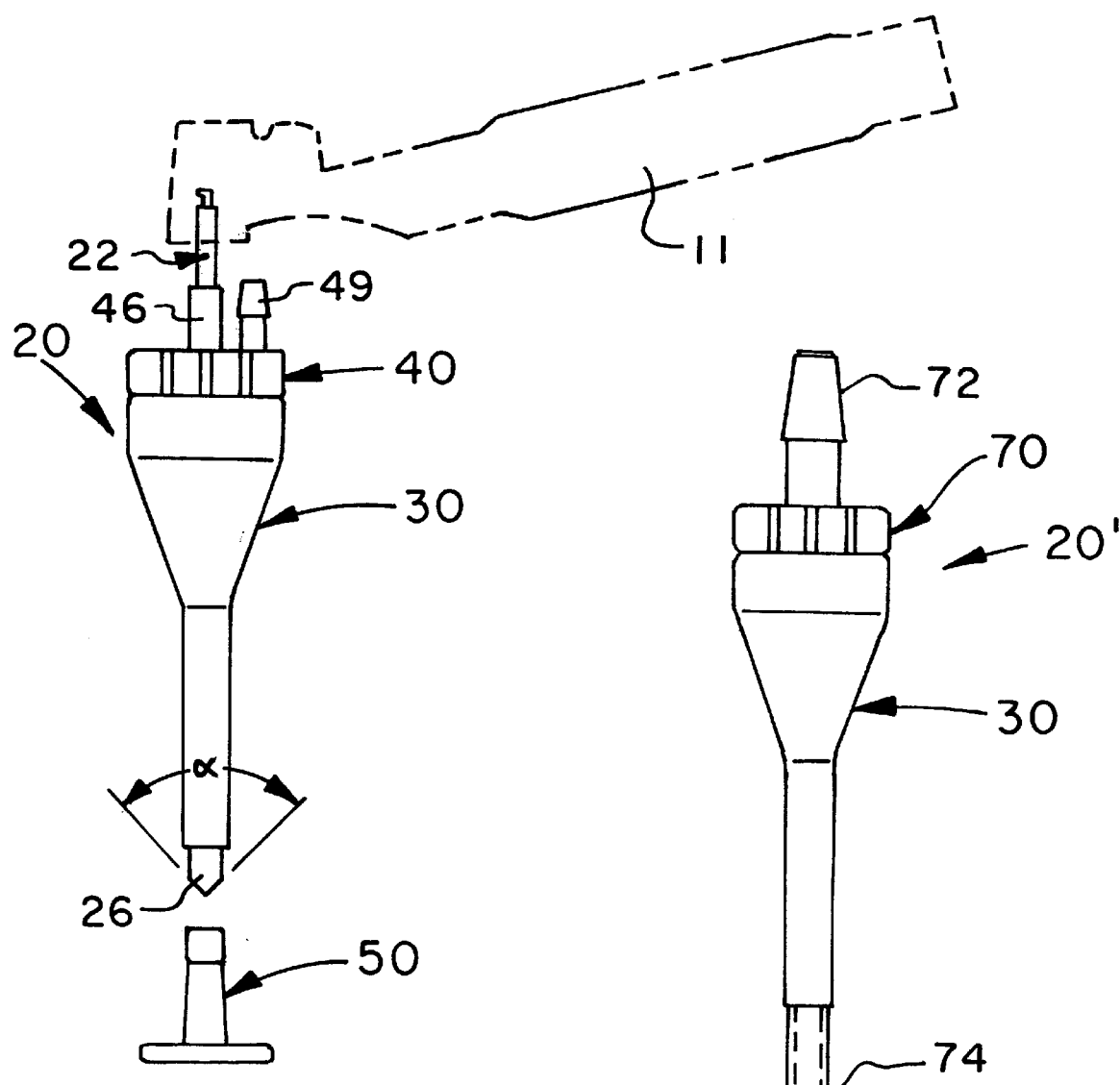

BONE HARVESTING COLLECTION AND DELIVERY SYSTEM

The present invention is directed to a device which can harvest bone from one site and deliver morselized bone fragments to another reparation site. More particularly, the present invention is directed to a bone harvest and delivery system that is capable of harvesting, morselizing, collecting and delivering bone fragments to a reparation site with a minimally invasive surgical incision.

BACKGROUND AND SUMMARY OF THE INVENTION

A number of devices are currently available for harvesting living bone tissue for reparative bone grafting procedures. Certain of these devices involve a manual scraping of bone from either the jaw or iliac crest of the hip of the patient. Significant portions of bone must be exposed in order to permit the necessary scraping motion. Other devices involve the use of a drill to create the bone fragments, then the collection of the particles by a secondary operation involving a different tool. Yet a third device involves carving out a window in the bone and introducing the harvested material into a table top grinder to morselize the fragment into particles of appropriate size. A fourth device, called a trephine or coring drill removes a plug and in a secondary operation, grinds the plug to the desired particle size.

It is an object of the present invention to overcome the deficiencies of the prior art by providing a single device which can harvest, morselize, collect and deliver bone particles to a reparative site in a single continuous procedure while requiring only a minimally invasive incision. In addition, an alternate cap and filter screen can be utilized to convert the system for collecting morselized fragments created by a previous drilling operation.

The bone harvesting, collection, and delivery system of the present invention includes a rotary drill bit adapted for attachment to a rotary surgical power tool. The drill bit preferably has a tip angle of 90° for maximum bone penetration and edges of the tip to cut and morselize the bone as the drill bit penetrates the designated area. The collection reservoir for collecting bone chips harvested by the drill bit includes an elongated body member and a removable top, said elongated body member having a tubular cannula portion which serves as a cylindrical guide for said drill bit and an enlarged chamber portion which receives the morselized bone fragments.

A suction port extends through said removable top into the enlarged chamber portion such that suction can be applied to a harvest site through said enlarged chamber portion and said tubular cannula portion so that bone fragments and irrigation fluid are removed from the harvest site by being drawn into a distal end of said tubular cannula portion. A fine mesh filter screen located in said collection reservoir filters the bone fragments from the irrigation fluid, the bone fragments being retained in said collection reservoir as the irrigation fluid is removed through said suction port. A retention plug may be inserted in said distal end of the tubular cannula portion to retain the bone fragments in the collection reservoir after said bone fragments have been harvested.

A plunger which can be inserted into said a top portion of the collection reservoir to eject said harvested bone fragments from said distal end of said tubular cannula portion into a reparation region. Preferably, the cap has threads which are on an external portion of its periphery which engage inwardly projecting threads of said collection reservoir. In this way, the cap has a profile which is no greater than that of the collection reservoir. The body and top of the reservoir are preferably made of a biocompatible material selected from the group consisting of titanium, alloys of titanium and a sturdy plastic material. Plastic is most preferable, since the use of a transparent or translucent plastic material will enable a visual determination of completion of the collection process without the need to remove the cap from the body of the collection reservoir.

A safety feature of the present device is that the depth of cut is limited. The cap has a guide tube which extends upwardly toward the power tool. The guide tube steadies the drill bit during its operation and, in addition, a leading end of the guide tube serves to stabilize the filter screen against the pull of the suction. The length of the drill bit and the bottoming out of the power tool against the top of the guide tube serve to limit the penetration depth of the drill bit. Preferably, the device will be sold with several lengths of drill bits since, for example, the penetration desired for harvesting from a jaw bone will generally be different from the penetration desired when harvesting from an iliac crest of a hip bone.

A collection cap equipped with a large suction port may supplant said harvesting cap and its drill bit to enable collection of bone fragments harvested by an earlier drilling operation. A collection wand is insertable into said distal end of said tubular cannula portion to enable collecting of bone fragments from such a harvest site. The collection wand has an angled portion proximate said distal end to facilitate insertion into a harvest site. The collection cap and wand can be removed and the plunger utilized to deliver bone fragments to the restoration site as was done with the earlier configuration.

Various other features, advantages and characteristics of the present invention will become apparent to one of ordinary skill in the art after a reading of the following specification.

BRIEF DESCRIPTION OF THE DRAWINGS

The preferred embodiment(s) of the present invention is/are described in conjunction with the associated drawings in which like features are indicated with like reference numerals and in which FIG. 1 is a side view of a first embodiment of the bone harvesting, collection, and delivery system of the present invention;

FIG. 4 is a side view of the bone harvesting, collection, and delivery system configured to collect bone fragments which have been harvested during an earlier drilling operation.

DETAILED DESCRIPTION OF THE PREFERRED EMBODIMENTS

Figure 2A:
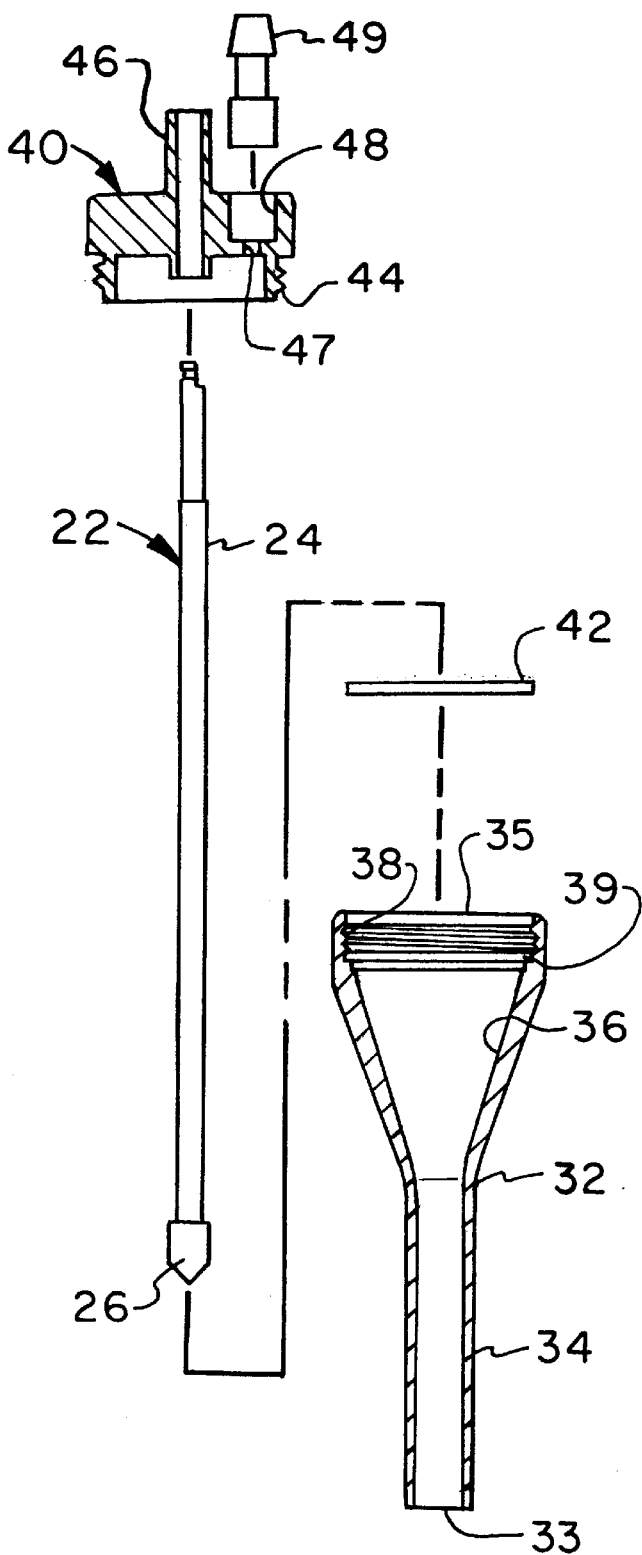
FIG. 2A is an exploded side view in partial section of the system shown in FIG. 1.
Figure 2B:
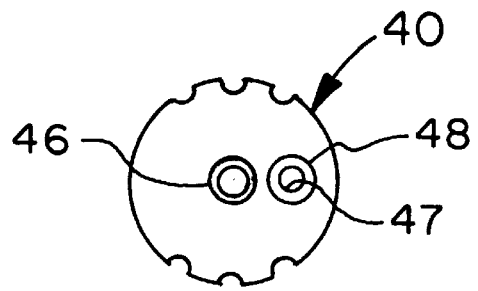
FIG. 2B is a top view of the cap of the collection reservoir of the present invention.
Figure 2C:
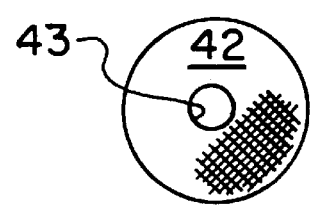
FIG. 2C is a top view of the filter screen used in the system of the present invention.

A first preferred embodiment of the bone harvesting, morselizing, collection, and delivery system of the present invention is shown in FIG. 1 generally at 20. As depicted in FIG. 1, the system comprises a drill bit 22, a collection reservoir 30 and a retention plug 50. As better seen in FIG. 2A, collection reservoir 30 includes an elongated body member 32 and a removable cap 40. Elongated body member 32 has tubular cannula portion 34 with distal end 33, and enlarged chamber 36 which receives morselized bone fragments. The top portion 35 of enlarged chamber 36 has inwardly directed threads 38. In addition, a seat or ledge 39 is provided to receive filter screen 42. Screen 42 has a central throughbore 43 which receives the shank 24 of drill bit 22. Drill bit 22 has a tip 26 with a tip angle α (FIG. 1) designed for optimum bone penetration. Experimentation has shown that the preferred design value range for α is between 80°–130°, with specific beneficial results at 90°.

Removable cap 40 is provided with externally threaded portion 44 which engage in threads 38 of chamber 36. By using external threads 44, the diameter of the cap 40 need not exceed the diameter of chamber 36. Cap 40 has a central guide tube 46 that performs two functions: first, tube 46 guides shank 24 of drill bit 22; and second, the upper end of tube 46 serves to limit the penetration of drill tip 26 into the bone by serving as a stop for the rotary surgical power tool 11. This in turn, limits the length drill tip 26 extends beyond distal end 33 and the depth it penetrates the bone. Adjacent guide tube 46 is throughbore 47 which is concentric with recess 48 which receives barbed fitting 49. A suction tube (not shown) can be connected to barbed fitting 49. The suction will draw bone fragments into distal end 33 of collection reservoir 30 along with irrigation fluid from the harvest site.

Filter screen 42 will allow irrigation fluid to removed from the enlarged chamber 36 while retaining harvested bone fragments therein. The leading end of guide tube 46 which is within chamber 36 engages screen 42 around the periphery of central throughbore 43, which along with the engagement by the leading edge of threaded portion 44 at the outer periphery of filter screen 42, stabilizes it against the upward pull of the suction force. The drill bit 22 of the present device 20 is intended to operate at speeds below 2000 rpm so as not to produce elevated temperatures at the harvest site or in the collection reservoir 30 which might kill the harvested tissue. The collection reservoir 30 and removable cap 40 are preferably made of biocompatible materials selected from the group including titanium, titanium alloys, and sturdy plastic material. It is preferred that a sturdy plastic be used for these components, and that the plastic be selected from those plastics which are transparent and translucent so that a visual check on the completion of the collection process can be made by viewing how full the chamber 36 is without the need for removing the cap 40.

When the harvesting of bone fragments is complete (for one application, the chamber 36 will hold 3 cubic centimeters (cc) of harvested tissue while for another application the chamber 36 can 10 hold anywhere from 20–40 cc's), the drill bit can be retracted within cannula 34 a sufficient distance to permit retention plug 50 to be inserted into distal end 33 while suction is still being applied to fitting 49. Once plug 50 is in place, suction can be halted, cap 40 removed so that filter screen 42 and drill bit 22 can be removed from the assembly and discarded. Screen 42 and bit 22 are intended to be single use items for health reasons, while the remaining components of the system can be sterilized and reused. With cap 40 removed, collection reservoir 30 can be used as a mixing vessel for addition of alloplast or additional protein and may be transported to the reparation site where plug 50 is removed. Tamping end 62 of plunger 60 may be inserted into the upper end 35 of chamber 36 and, by manipulating enlarged handle 64, tamping end 62 can deliver bone fragments out distal end 33 of cannula 34.

Figure 5:
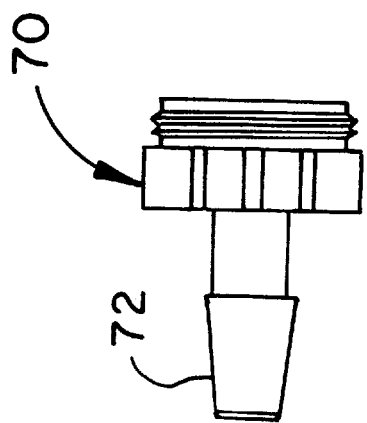
FIG. 5 is a side view of the collection cap used to perform the subsequent collection.
Figure 3:
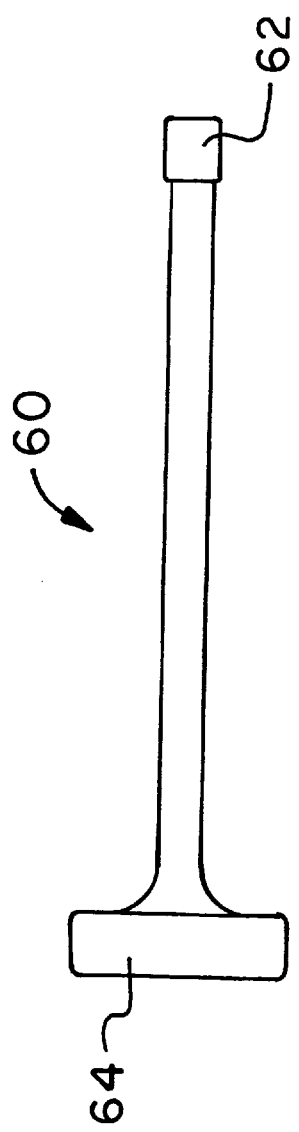
FIG. 3 is a side view of the tamper used to deliver harvested bone fragments to a reparation site.

The bone harvesting, collection and delivery system 20 of the present invention has the flexibility to be used to collect morselized bone fragments which have been previously harvested by a separate drilling operation. To facilitate this collection, harvesting cap 40 is replaced by a collection cap 70 (FIGS. 4 and 5). Collection cap 70 has a centrally located suction port 72 which is larger than its offset counterpart in the harvesting cap 40. Since in this configuration, system 20' is used without a drill, screen 42 can be replaced by a solid screen that has no throughbore. Collection system 20' is equipped with a collection wand 74 which is frictionally received in the distal end 33 of cannula 34. Wand 74 has a knee 76 toward its leading end 77 which produces an angled section 78. This angled section 78 facilitates the collection process by getting the system 20' out of the line of sight of the physician to provide a better view of the harvest site.

The bone harvesting, collection, and delivery system 20 of the present invention enables bone fragments to be intraorally harvested (or retrieved from an alternate site such as the iliac crest), morselized, collected and delivered to a reparation site utilizing only a minimally invasive surgical incision with a single device in one continuous procedure. Alternatively, the present device can be converted into a collection system 20' to collect bone fragments harvested by a separate earlier drilling procedure.

Various changes, alternatives and modifications will become apparent to one of ordinary skill in the art following a reading of the foregoing specification. It is intended that any such changes, alternatives and modifications as fall within the scope of the appended claims be considered part of the present invention.

We claim:

1. A bone harvesting, collection, and delivery system comprising
    a) a drill bit adapted for attachment to a rotary surgical power tool for cutting and morselizing a bone which it engages creating morselized bone fragments;
    b) a collection reservoir for collecting bone fragments harvested by said drill bit, said collection reservoir having an elongated body member and a removable harvesting cap, said elongated body member having a tubular cannula portion which serves as a cylindrical guide for said drill bit and an enlarged chamber portion which receives the morselized bone fragments;
    c) a suction port extending through said harvesting cap into said enlarged chamber portion such that suction can be applied to a harvest site through said enlarged chamber portion and said tubular cannula portion so that bone fragments and irrigation fluid are removed from the harvest site by being drawn into a distal end of said tubular cannula portion;
    d) a fine mesh screen located in said collection reservoir which filters said bone fragments from said irrigation fluid, said bone fragments being retained in said collection reservoir as said irrigation fluid is removed through said suction port.

2. The bone harvesting, collection, and delivery system of claim 1 further comprising a retention plug which may be inserted in said distal end of said tubular cannula portion to retain the bone fragments in said collection reservoir after the bone fragments have been harvested.

3. The bone harvesting, collection, and delivery system of claim 1 further comprising a plunger which can be inserted into a top portion of the collection reservoir to eject said harvested bone fragments from said distal end of said tubular cannula portion into a reparation region.

4. The bone harvesting, collection, and delivery system of claim 1 wherein said removable harvesting cap is threadably attached to said collection reservoir.

5. The bone harvesting, collection, and collection system of claim 4 wherein said removable harvesting cap has threads which are on an external portion of its periphery which engage inwardly projecting threads of said collection reservoir.

6. The bone harvesting, collection and delivery system of claim 5 wherein said removable harvesting cap further comprises a guide tube which is coaxial with said tubular cannula portion of said collection reservoir, said guide tube assisting in guiding the drill bit.

7. The bone harvesting, collection, and delivery system of claim 1 wherein said removable harvesting cap and said collection reservoir are each made of biocompatible material.

8. The bone harvesting, collection, and delivery system of claim 7 wherein said biocompatible material is selected from the group consisting of titanium, alloys of titanium and a sturdy plastic material.

9. The bone harvesting, collection, and delivery system of claim 8 wherein said plastic material is selected from among plastics which are transparent and translucent whereby a fullness of said collection reservoir can be visually monitored through said plastic.

10. The bone harvesting, collection, and delivery system of claim 1 wherein a depth of cut of the drill bit is limited by an amount the drill bit extends beyond said distal end of said tubular cannula portion of said collection reservoir as permitted by the rotary surgical power tool contacting said guide tube.

11. The bone harvesting, collection, and delivery system of claim 1 wherein said drill bit has a tip portion having an included angle designed for optimum bone penetration and cutting edges which both cut and morselize the bone as said edges are rotated.

12. The bone harvesting, collection, and delivery system of claim 11 wherein said included angle for optimum bone penetration comprises an angle of 90°.

13. The bone harvesting, collection, and delivery system of claim 1 further comprising a collection cap equipped with a large suction port which may supplant said harvesting cap and its drill bit to enable collection of bone fragments harvested by an earlier drilling operation.

14. The bone harvesting, collection, and delivery system of claim 13 further comprising a collection wand insertable into said distal end of said tubular cannula portion to enable collecting of bone fragments from the harvest site, said bone fragments having been produced by said earlier drilling operation.

15. The bone harvesting, collection, and delivery system of claim 14 wherein said collection wand has an angled portion proximate said distal end to facilitate insertion into a harvest site.

* * * * *